United States Patent
Sudo et al.

(10) Patent No.: US 6,628,379 B1
(45) Date of Patent: Sep. 30, 2003

(54) METHOD AND APPARATUS FOR INSPECTION OF RUBBER PRODUCT

(75) Inventors: Masamichi Sudo, Tokyo (JP); Morihiro Sudo, Tokyo (JP)

(73) Assignee: Daiko Seiko Ltd., Tokyo (JP)

(*) Notice: Subject to any disclaimer, the term of this patent is extended or adjusted under 35 U.S.C. 154(b) by 0 days.

(21) Appl. No.: 09/329,390

(22) Filed: Jun. 10, 1999

(30) Foreign Application Priority Data

Sep. 30, 1998 (JP) .......................................... 10-278648

(51) Int. Cl.$^7$ .............................................. G01N 21/00
(52) U.S. Cl. ............................... 356/237.1; 356/238.1; 356/239.1; 250/562; 250/223 B
(58) Field of Search ................................ 356/128–136, 356/237.1–237.4, 238.1–238.3, 239.1, 239.8; 250/223 B, 223 R, 561, 562, 563; 382/141

(56) References Cited

U.S. PATENT DOCUMENTS

| | | | |
|---|---|---|---|
| 3,715,476 A | * | 2/1973 | Watanabe et al. |
| 4,389,575 A | * | 6/1983 | Code .......................... 356/430 |
| 4,467,214 A | * | 8/1984 | Ito et al. ................... 356/237.1 |
| 4,543,602 A | * | 9/1985 | Kai et al. .................... 356/128 |
| 5,329,133 A | * | 7/1994 | Uesugi et al. ............ 356/239.1 |
| 5,452,079 A | * | 9/1995 | Okugawa ................. 356/237.1 |
| 5,598,262 A |   | 1/1997 | Jutard et al. ................ 356/239 |
| 5,666,199 A | * | 9/1997 | Hess et al. .................. 356/430 |
| 5,691,811 A | * | 11/1997 | Kihira ...................... 356/237.1 |
| 5,974,167 A | * | 10/1999 | Reszler ........................ 382/141 |
| 6,011,620 A | * | 1/2000 | Sites et al. ................ 356/239.1 |
| 6,396,579 B1 | * | 5/2002 | Hayamizu et al. ........ 356/239.7 |

FOREIGN PATENT DOCUMENTS

| | | | |
|---|---|---|---|
| DE | 36 11 574 A | | 10/1987 |
| DE | 279 828 A | | 6/1990 |
| DE | 297 07 985 | | 7/1997 |
| JP | 03 113 352 | * | 5/1991 |
| JP | 07 043314 A | | 2/1995 |
| JP | 07 159 348 | * | 6/1995 |
| JP | 2000 346 813 | * | 12/2000 |

\* cited by examiner

*Primary Examiner*—Frank G. Font
*Assistant Examiner*—Sang H. Nguyen
(74) *Attorney, Agent, or Firm*—McCormick, Paulding & Huber LLP

(57) ABSTRACT

A rubber product inspection method for inspecting internal flaws and/or surface defects of a vulcanized transparent or translucent rubber product includes: irradiating illumination light onto the rubber product, so that the light transmitted through the rubber product can be picked-up; and determining an absence or presence of internal flaws of the rubber product, based on an image of the transmitted light picked-up by an image pickup device. An inspection apparatus for executing the inspection method includes a transparent or translucent table on which the rubber product in placed; at least one light source and an image pickup CCD camera which are provided on opposite sides of the table.

6 Claims, 3 Drawing Sheets

METHOD AND APPARATUS FOR INSPECTION OF RUBBER PRODUCT

BACKGROUND OF THE INVENTION

1. Field of the Invention

The present invention relates to a method and apparatus for inspecting defects of a rubber product, such as a rubber plug for use in medical supplies or medical implements, or for inspecting defects in a rubber sheet.

2. Description of the Related Art

For plugs used in medical supplies or medical implements, not only must surface flaws, such as surface marks or stains, etc., be examined in accordance with sanitary and safety requirements to prevent contamination by foreign matter, but also internal flaws, such as embedded foreign matter. If we ignore the inefficiency drawback, surface flaws can be detected by visual inspection; however, internal flaws cannot be detection by such a method.

SUMMARY OF THE INVENTION

The primary object of the present invention is to provide an inspection method and apparatus in which internal flaws of a rubber product can be examined.

Another object of the present invention is to provide an inspection method and apparatus in which surface flaws and internal flaw of a rubber product can be examined simultaneously.

In order to achieve the above mentioned objects, there is provided a rubber product inspection method for inspecting internal flaws of a vulcanized rubber product, the rubber product having light-transmitting properties, wherein the method includes: irradiating illumination light onto the rubber product, so that the light transmitted through the rubber product can be picked-up by an image pickup device; and detecting internal flaws in the rubber product, based on an image of the transmitted light picked-up by the image pickup device.

Alternatively, there is provided a rubber product inspection method for inspecting internal flaws and surface defects of a vulcanized rubber product, the rubber product having light-transmitting properties, wherein the method includes: irradiating illumination light onto the rubber product, so that the light transmitted through the rubber product can be picked-up by an image pickup device; irradiating illumination light onto the rubber product, so that the light reflected by the rubber product can be picked-up by the image pickup device; detecting internal flaws in the rubber product, based on an image of the transmitted light picked-up by the image pickup device; and detecting surface defects on the rubber product, based on an image of the reflected light picked-up by the image pickup device.

Alternatively, there is provided a rubber product inspection apparatus including: a table on which a vulcanized rubber product is placed, the rubber product and the table having light-transmitting properties; light sources above and below the table, for producing reflected light and transmission light; and an image pickup CCD camera which is provided on the same side of the table as the light source for the reflected light; the image pickup CCD camera receiving the light emitted from the light source for the transmission light which is transmitted through the rubber product, and receiving the light emitted from the light source for the reflected light which is reflected by the rubber product.

Preferably, the light source for producing transmission light and the light source for producing reflected light are turned ON at different times.

Alternatively, there is provided a rubber product inspection apparatus including: a table on which a rubber product of vulcanized rubber material is placed, the table and the rubber material having light-transmitting properties; a light source which is provided on one side of the table, for producing transmission light; and an image pickup CCD camera which is provided on the other side of the table and which receives the light emitted from the light source for the light transmitted through the rubber product.

The rubber product can be a rubber plug for use in medical supplies or medical implements. Alternatively, the rubber product can be a rubber sheet.

The present disclosure relates to subject matter contained in Japanese Patent Application No. 10-278648 (filed on Sep. 30, 1998) which is expressly incorporated herein by reference in its entirety.

BRIEF DESCRIPTION OF THE DRAWINGS

The invention will be discussed below in detail with reference to the accompanying drawings, in which.

DESCRIPTION OF THE PREFERRED EMBODIMENT

Figure 1:
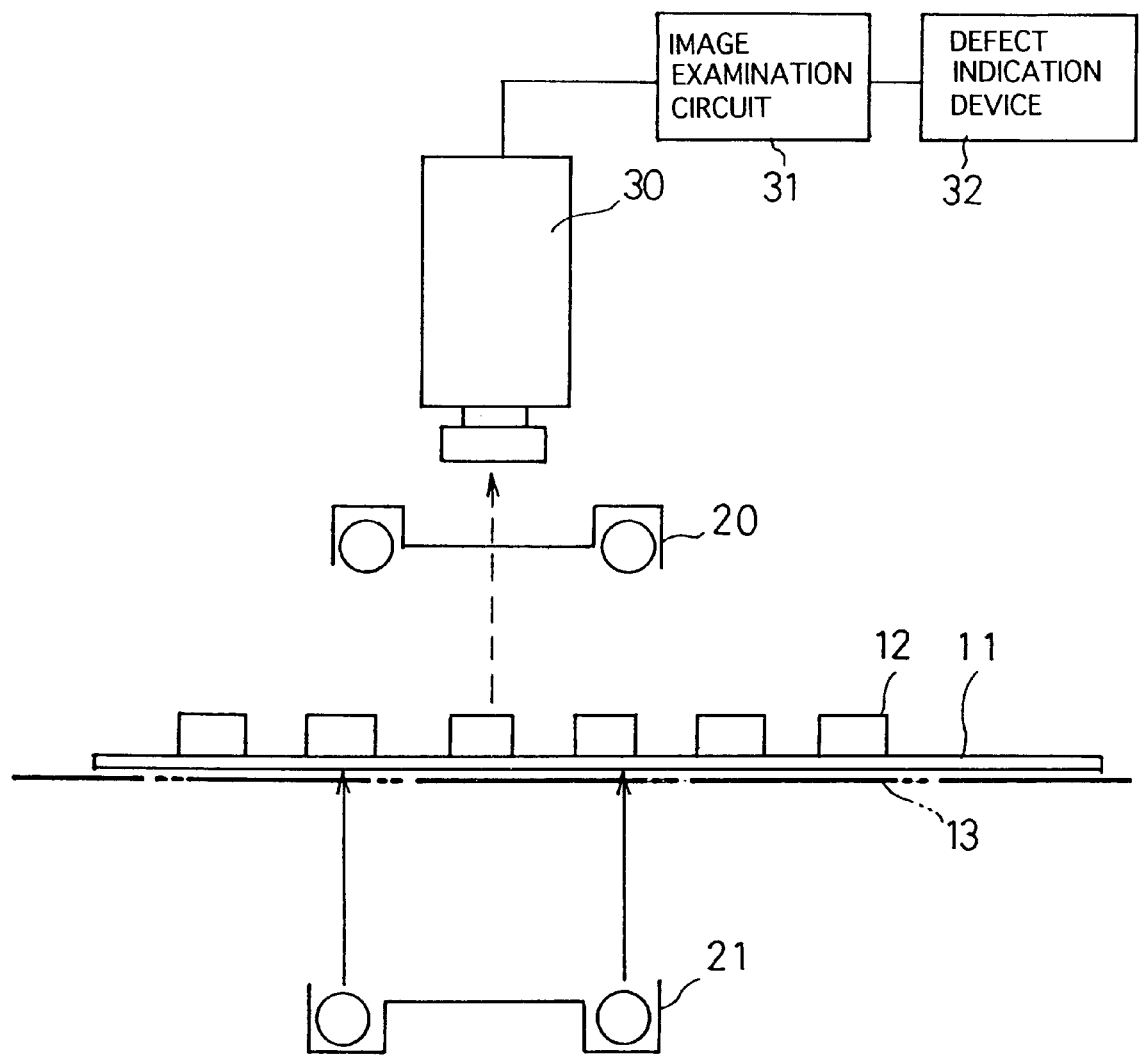
FIG. 1 is a conceptual view of an inspection method and apparatus for a rubber product, according to the present invention.

In the illustrated embodiment, a rubber product made of a transparent or translucent rubber material (a rubber material having light-transmitting properties) is in the form of a rubber plug 12 for use in medical supplies or medical implements. A number of rubber plugs 12 are integrally vulcanized on a substrate 11. Various kinds of transparent or translucent rubber materials are known, and a type appropriate for use in medical supplies or medical implements is selected. The rubber material of which the substrate 11 and the rubber plugs 12 are made may be mixed with an inorganic reinforcing agent or coloring agent, but it is preferable that such a reinforcing agent or coloring agent not be used in order to possess maximum transparency.

A plurality of rubber plugs 12 are positioned upward on the substrate 11, the substrate 11 being placed on a transparent or translucent table 13. The table 13 is not limited to a specific shape so long as illumination light can be uniformly irradiated onto the rubber plugs 12. Moreover, the table 13 can be either movable or immovable.

Above and below the table 13 are provided a light source 20 for reflected light and a light source 21 for transmission light, respectively. The light sources 20 and 21 are each made of an annular lighting element having a center opening. A CCD camera 30 is provided in the center opening of the light source 20 for reflected light. The CCD camera 30 is arranged so as to receive the light emitted from the light source 20 and reflected by the substrate 11 and the rubber plugs 12, and the light emitted from the light source 21 and transmitted through the substrate 11 and the rubber plugs 12. The CCD camera 30 is connected to an image examination circuit 31 which is in turn connected to a defect indication device 32. The CCD camera 30 for recognizing an image pattern is known in the art.

Figure 2:
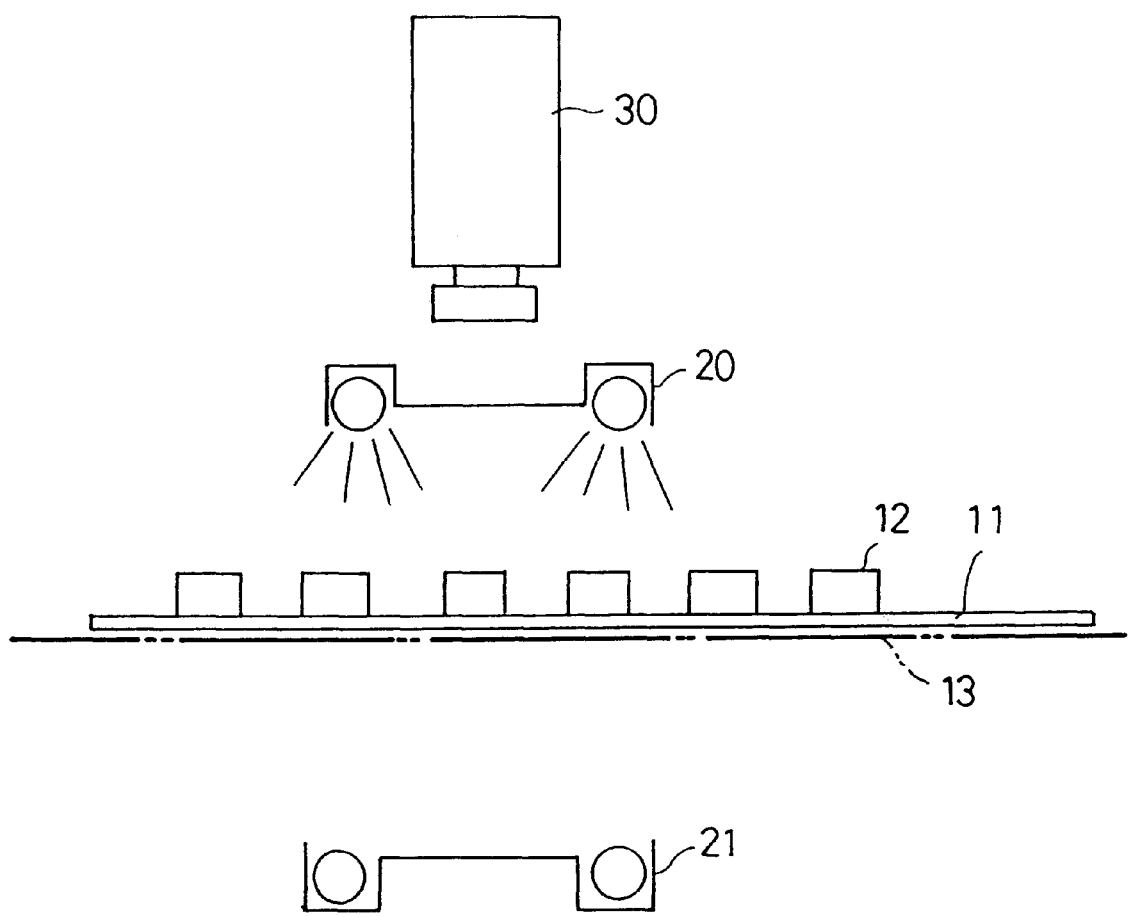
FIG. 2 is a conceptual view of another inspection process in an inspection apparatus shown in FIG. 1.

In the apparatus construction described above, the light sources 20 and 21 are turned ON at different times to emit light by a first and a second step, so that the image is picked up by the CCD camera 30 and is examined by the image examination circuit 31 to examine surface defects and internal flaws of the rubber plugs 12. Namely, in the first step, the light source 20 to produce reflected light is activated to illuminate the substrate 11 and the rubber plugs 12, and the light reflected by the substrate 11 and the rubber plugs 12 is picked-up by the CCD camera 30, as shown in FIG. 2. The second step is carried out at a different timing from the first step, in which the light source 21 to produce transmission light is activated to illuminate the substrate 11 and the rubber plugs 12 with the illumination light, and the light transmitted through the substrate 11 and the rubber plugs 12 is picked-up by the CCD camera 30, as shown in FIG. 1. The order of the first and second step can be changed.

Figure 3:
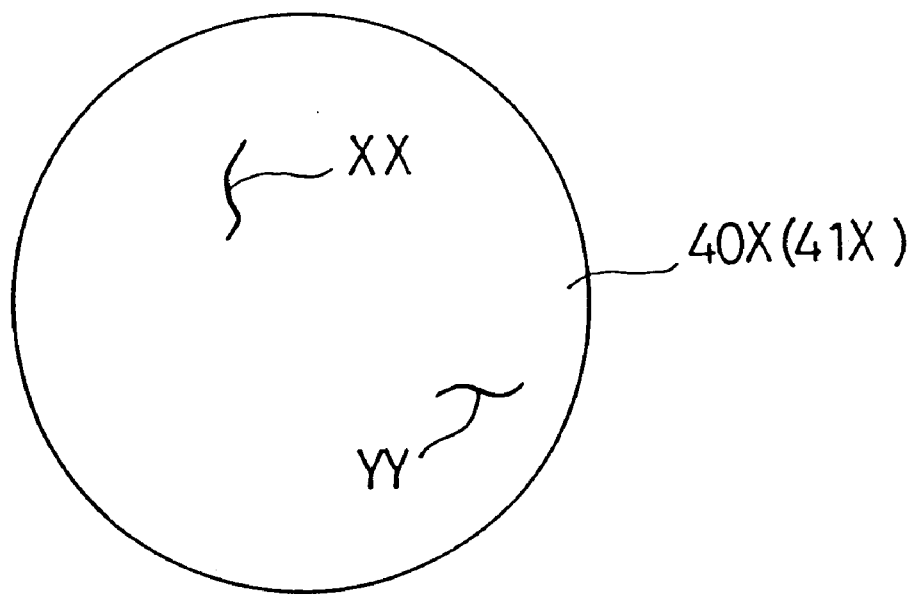
FIG. 3 is a schematic view of samples of an image formed by transmission light (or reflected light) and a correct image, by way of example.
Figure 3:
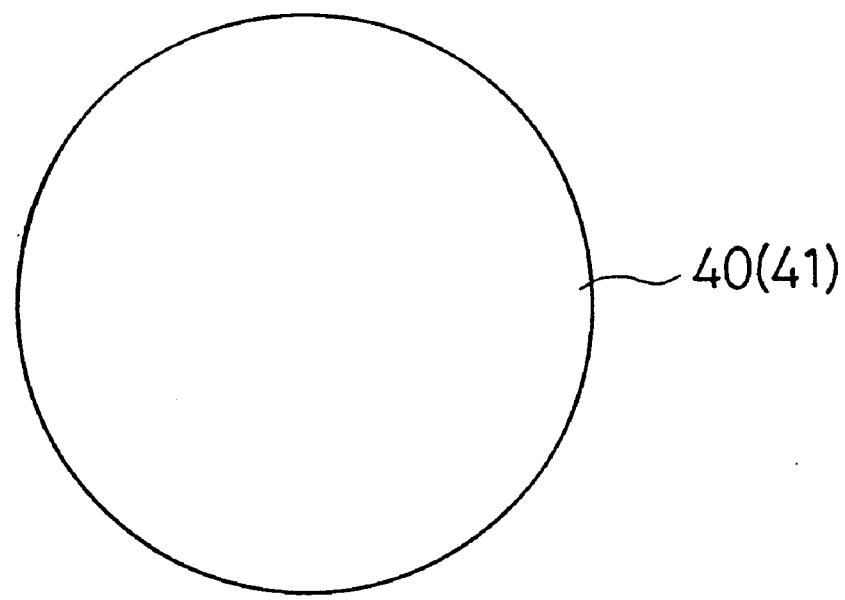

The image examination circuit 31 has pre-stored therein flawless images formed by the reflected light and by the transmission light using a flawless substrate 11 and rubber plugs 12 which have no surface defects or no internal flaws. The presence or absence of the defects can be determined via pattern recognition technology. For example, as schematically shown in FIG. 3, the image examination circuit 31 compares the stored flawless image 40 formed by the reflected light with the actual image 40X of the rubber plugs 12 under examination formed by the reflected light. Similarly, the image examination circuit 31 compares the stored flawless image 41 formed by the transmission light with the actual image 41X of the rubber plugs 12 under examination formed by the transmission light. If the reflection light image 40X or the transmission light image 41X contains a defect XX or YY as shown in FIG. 3, it is determined that the rubber plugs 12 contain a surface defect or an internal flaw, which is indicated by the defect indication device 32. The pattern recognition technology as described herein is known in the art.

If the examination shows that there is no surface defect or internal flaw, the rubber plugs 12 are moved to a subsequent stage in which the rubber plugs 12 are cut and separated from the substrate 11 to obtain rubber products. The rubber plugs 12 which are determined as defective are rejected.

It is possible to indicate the surface defects and the internal flaws separately or without distinguishing them. If the rubber plug 12 contains a surface defect or an internal flaw, the plug is usually rejected. Therefore, in general, it is not necessary to distinguishably indicate the surface defect and the internal flaw. However, for example, if the surface defect can be removed or repaired, it would be useful to distinguishably indicate a surface defect from an internal flaw. Separate indication is also useful to determine a defective portion of a vulcanization line.

The above discussion has been addressed to the simplest inspection method and apparatus according to the present invention. The illustrated embodiment can be modified. For example: the image pickup operation of the rubber plugs 12 by the CCD camera 30 can be carried out while moving the table 13; a plurality of images of the rubber plugs 12 can be picked-up by one image pickup operation; an indicia or mark, etc., can be printed on a defective plug 12 by a printer; the defective plug 12 can be cut and removed from the substrate 11 at the subsequent stage and thereafter, the good products are cut in a subsequent step.

Furthermore, the oscillation wavelength of the reflection light source 20 can be different from the oscillation wavelength of the transmission light source 21, depending on the transmittance or reflectance of the substrate 11 and the rubber plugs 12.

In the embodiment mentioned above, rear surface defects of the substrate 11 are not inspected. If the surface defect on the rear surface (rear surface in FIGS. 1 and 2) of the substrate 11 should be also examined, the surface is irradiated with the illumination light emitted from the reflection light source, so that the light reflected thereby can be received by the CCD camera to carry out the same image examination as above.

As can be understood from the above discussion, internal defects of a rubber product can be examined. Moreover, since the surface defects can be also examined in addition to the internal defects, a full examination can be carried out. Furthermore, the inspection method can be executed by a simple inspection apparatus.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. A rubber product inspection method for inspecting internal flaws and surface defects of a vulcanized rubber product, said rubber product having light-transmitting properties, wherein said method comprises:

a first step of irradiating illumination light onto said rubber product, so that the light transmitted through said rubber product can be picked-up by an image pickup device;

a second step of irradiating illumination light onto said rubber product, so that the light reflected by said rubber product can be picked-up by said image pickup device;

wherein said first and said second steps take place at a different times;

detecting internal flaws in the rubber product, based on a two-dimensional image of the transmitted light picked-up by said image pickup device; and detecting surface defects on the rubber product, based on an image of the reflected light picked-up by said image pickup device.

2. A rubber product inspection method according to claim 1, wherein said rubber product is a rubber plug for use in medical supplied or medical implements.

3. A rubber product inspection method according to claim 1, wherein said rubber product is a rubber sheet.

4. A rubber product inspection apparatus comprising:

a table on which a vulcanized rubber product is placed, said rubber product and said table having light-transmitting properties;

a first light source provided on one side of said table for producing reflected light;

a second light source provided on the other side of said table for producing transmission light;

wherein said first light source for producing transmission light and said second light source for producing reflected light are turned ON at different times; and an image pickup CCD camera provided on the same side of said table as the first light source for the reflected light; said image pickup CCD camera receiving the light emitted from the second light source for the transmission light which is transmitted through the rubber product and sensing a two-dimensional image derived from the transmission light received, and receiving the light emitted from the first light source for the reflected light which is reflected by the rubber product and sensing an image derived from the reflected light received.

5. A rubber product inspection apparatus according to claim 4, wherein the rubber product is a rubber plug for use in medical supplies or medical implements.

6. A rubber product inspection apparatus according to claim 4, wherein said rubber product is a rubber sheet.

* * * * *